United States Patent [19]

Gelo et al.

[11] Patent Number: 4,661,236
[45] Date of Patent: Apr. 28, 1987

[54] FLUID ELECTRODE AND METHOD OF MAKING

[75] Inventors: Mark A. Gelo, Concord; Moshe J. Hirshberg, Brookline, both of Mass.; Lionel S. Goldring, Woodbridge, Conn.

[73] Assignee: Orion Research, Inc., Cambridge, Mass.

[21] Appl. No.: 547,378

[22] Filed: Oct. 28, 1983

[51] Int. Cl.[4] ..................... G01N 27/26; C03B 23/20; H01R 43/00

[52] U.S. Cl. ..................... 204/420; 65/138; 65/36; 65/40; 65/59.25; 29/825

[58] Field of Search ......... 29/593, 595, 825; 65/36, 40, 59.25, 59.31, 102, DIG. 6; 204/416-420; 219/121 LE, 121 LF, 121 LM, 121 EM

[56] References Cited

U.S. PATENT DOCUMENTS

| | | | |
|---|---|---|---|
| 3,217,088 | 11/1965 | Steierman | 65/40 X |
| 3,444,068 | 5/1969 | Leonard et al. | 204/420 |
| 3,523,777 | 8/1970 | Petersen et al. | |
| 3,660,064 | 5/1972 | Rohde | 65/40 X |
| 3,741,884 | 6/1973 | Deushane et al. | 204/420 |
| 3,749,562 | 7/1973 | Nicolas et al. | 65/36 X |
| 3,855,095 | 12/1974 | Leonard et al. | 65/40 X |
| 3,876,409 | 4/1975 | Sangermang et al. | 65/40 |
| 4,182,668 | 1/1980 | Koshiishi et al. | 204/417 |

*Primary Examiner*—Howard N. Goldberg
*Assistant Examiner*—Carl J. Arbes
*Attorney, Agent, or Firm*—Cesari and McKenna

[57] ABSTRACT

An improved electrode for detecting ion concentration and a method of manufacturing such an electrode. The electrode includes concentric glass tubes, including an inner tube which is filled with a filling solution and a larger, outer tube which extends above the level of the filling solution in the inner tube. A metal contact is immersed in the filling solution and extends outside the inner tube through a hermetic seal to allow electrical contact to be made to the filling solution. The inner tube is made of a different glass from the outer tube so that the inner tube will absorb radiation at selected wavelengths which are transmitted by the outer tube. The inner tube is illuminated with radiation of the proper wavelength so that the inner tube melts and collapses around the metal contact to form the hermetic seal. In an alternate embodiment, the electrode has an inner tube which is made of two different types of glass. An apparatus for mechanizing the electrode sealing process is also described.

20 Claims, 12 Drawing Figures

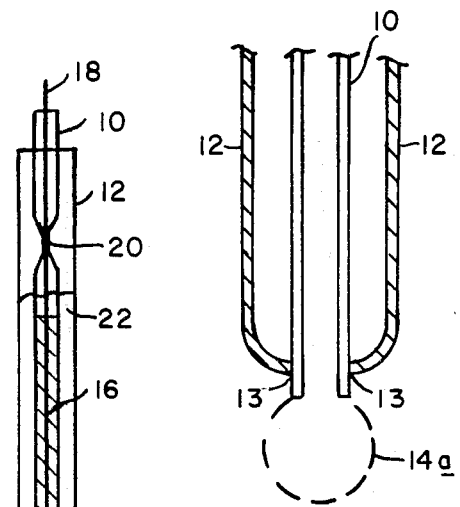
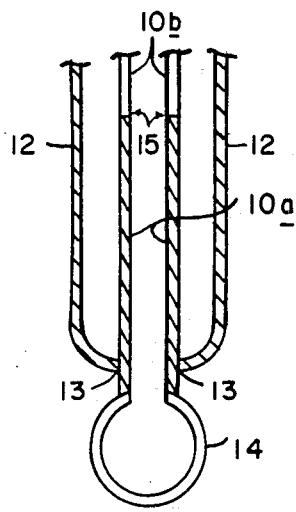
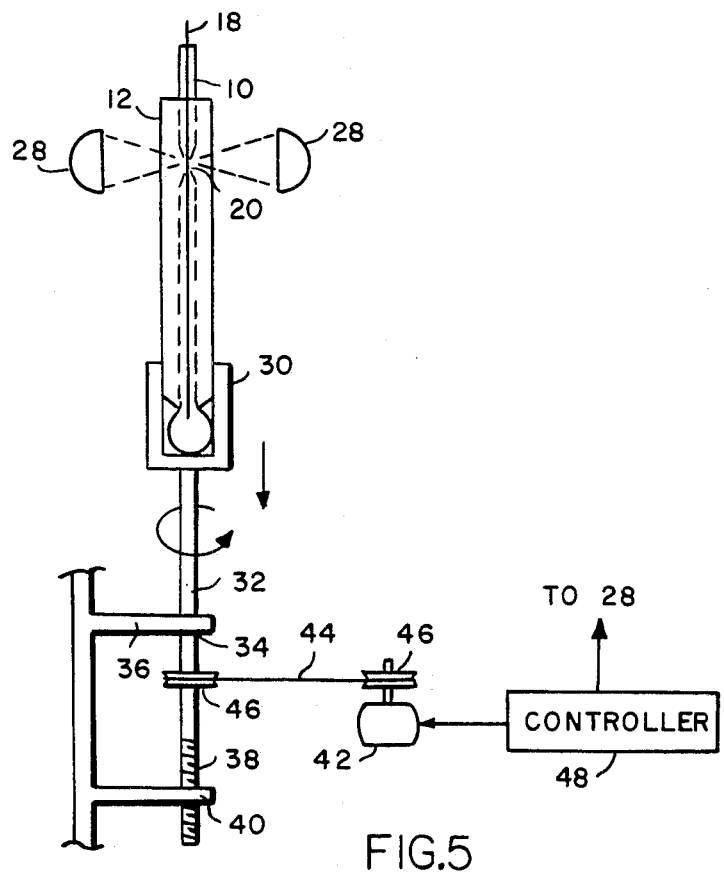

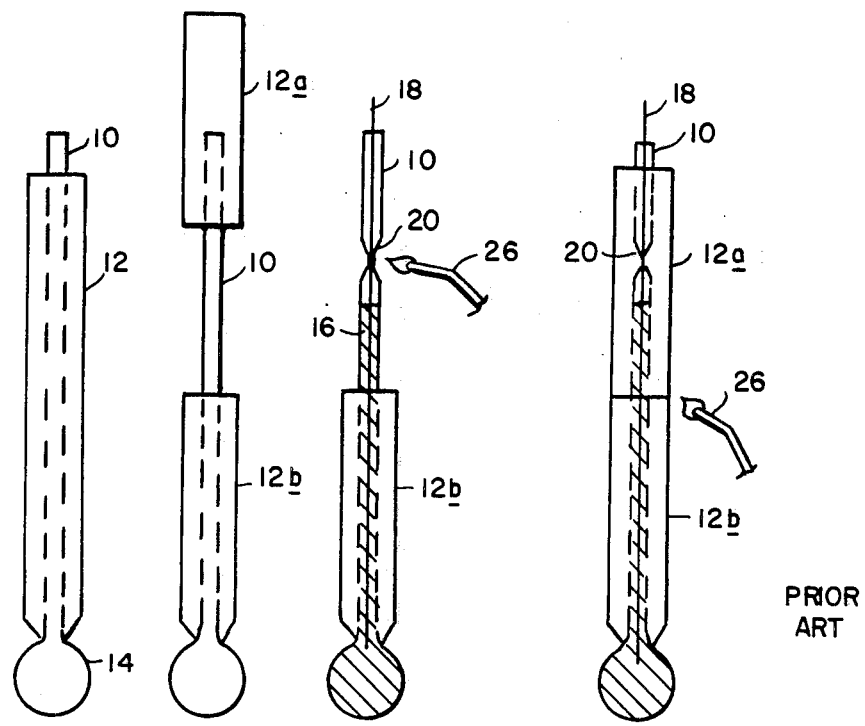
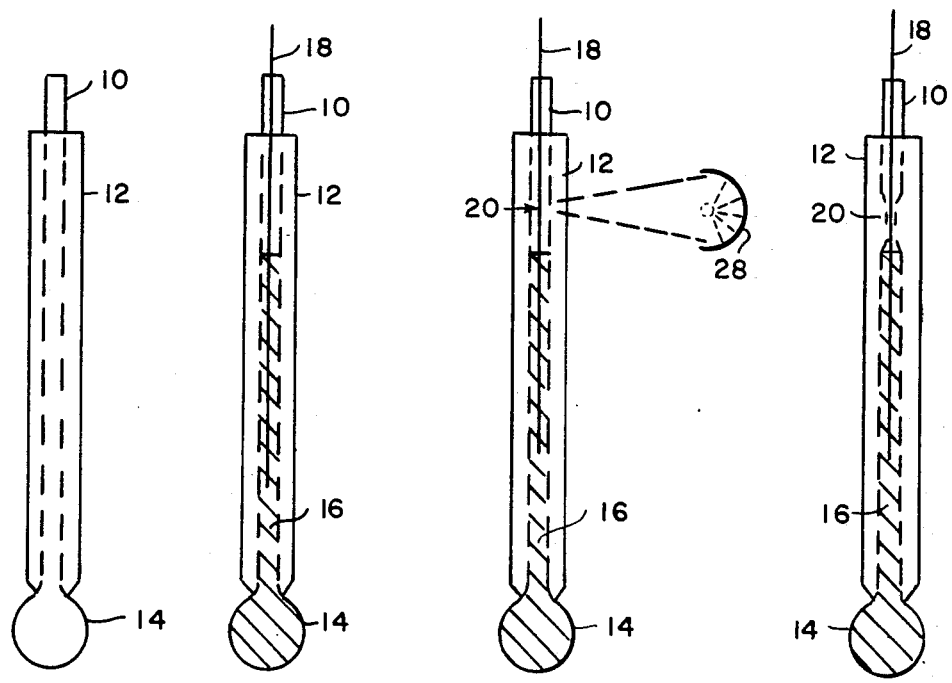

FLUID ELECTRODE AND METHOD OF MAKING

FIELD OF THE INVENTION

This invention is related to the fabrication of glass encapsulated fluid electrodes, and more particularly to the fabrication of fluid electrodes used to detect and measure ion concentrations.

BACKGROUND OF THE INVENTION

The measurement of properties of liquid and gaseous fluids by detecting a voltage produced by a sensor is a common problem in research and in industrial processes. The measurement of ion concentrations of fluid solutions is a typical example and utilizes ion selective electrodes having one or more electrodes which are immersed in a chemical solution.

In one common type of ion selective electrode, the ion concentration is sensed by an electrode having a glass membrane. A tube is attached to the membrane and is filled with a filling solution. A metal wire is inserted in the top of the tube to provide an electrical contact to the filling solution. The filling solution must be hermetically sealed inside the tube and, a hermetic seal is typically made by melting the tube until it collapses around the metal contact after the tube has been filled with the solution.

As will be discussed in more detail below, present methods for fabricating the electrode, especially the making of the seal, require glass workers with a high degree of skill. Furthermore, even with highly skilled workers, a significant number of defective electrodes is to be expected.

SUMMARY OF THE INVENTION

The present invention includes an improved sensor for measuring properties of fluids and a method of manufacturing such a sensor. The present invention is especially applicable to electrodes used in detecting ion concentrations, although it is applicable to other similar sensors, for example, conductivity and temperature sensors.

Briefly, in the present invention the electrode or sensor is composed of concentric glass tubes, including an inner tube which is filled with a filling solution and a larger, outer tube which extends above the level of the filling solution in the inner tube. A metal contact is immersed in the filling solution and extends outside the inner tube to allow electrical contact to be made to the filling solution, and a hermetic seal is made by melting the inner tube around the contact. The inner tube is made of a different glass from the outer tube so that the inner tube will absorb radiation at selected wavelengths which are transmitted with little or no absorbsion by the outer tube. By exposing the inner tube with radiation of the proper wavelength, the inner tube is heated until it melts, and a hermetic seal may be quickly and reliably made around the metal contact. An alternate embodiment of the electrode has an inner tube which is made of two different types of glass to avoid problems caused by absorption of infrared radiation from molten glass when the membrane is formed at the end of the inner tube. An apparatus for mechanizing the electrode sealing process is also described.

DESCRIPTION OF THE DRAWINGS

The advantages and operation of the present invention will be more clearly understood by reading the following description of the preferred invention with reference to the drawings, of which:

FIG. 1 shows a typical type of ion selective electrode;

FIGS. 2A–2D show the prior art method of manufacturing the electrode of FIG. 1;

FIGS. 3A–3D illustrate one method for fabricating an electrode in accordance with the present invention;

FIGS. 4A and 4B show an improvement to the electrode of the present invention; and FIG. 5 shows an apparatus which may be used to manufacture the electrode in accordance with the present invention.

DESCRIPTION OF THE PREFERRED EMBODIMENT

FIG. 1 shows a typical electrode used in measuring ion concentration. In FIG. 1, an inner glass tube 10 lies within an outer glass tube 12. Inner tube 10 is terminated at its lower end in a glass bulb 14. Bulb 14 is fabricated from a special glass and forms a membrane, across which the ions to be measured generate a potential that is proportional to the ion activity gradient across the membrane. Tube 10 and bulb 14 contain a filling solution 16. The formulation of filling solution 16 depends upon the particular ions to be detected by the electrode. A metal contact 18, typically made of platinum or another noble metal is submersed in the filling solution to provide an electrical contact to the filling solution 16.

Contact 18 passes through a seal 20 which hermetically seals the filling solution within inner tube 10 and bulb 14. The space between the inner tube 10 and the outer tube 12 may be filled with another liquid solution 22, depending on the particular application of the electrode. To measure the ion concentration of a liquid solution, the bulb 14 of the electrode is submerged in the liquid to be measured. The ion concentration is determined by measuring electrical potential between contact 18 and a reference electrode immersed in the solution. The reference electrode may be placed in the area between the inner and outer tubes.

The filling solution is susceptible to picking up electrical signals which interfere with the measurement of ion concentration. Shielding is usually provided around the filling solution to reduce interference. This shielding may be provided by a liquid filling the area between the inner and outer tubes, by a thin metal shield between the inner and outer tubes, or by other means. Thus, the outer tube should extend above the level of the filling solution and the seal 20 inside inner tube 10.

The conventional manner of making the electrode of FIG. 1 is illustrated by FIGS. 2A–2D. The inner tube 10 is attached to the outer tube 12 and to bulb 14 prior to filling the inner tube with the filling solution and inserting contact 18, as shown by the structure of FIG. 2A. The manner in which this is done is described in more detail below. Next, the outer tube 12 is separated into two sections to expose the section of inner tube 10 where the seal 20 is to be formed. This is shown in FIG. 2B where the outer tube has been separated into two sections 12a and 12b.

When the top part of the inner tube has been removed, the inner tube is filled with the filling solution 16, and the metal contact 18 is inserted. Contact 18 is typically made of platinum or another noble metal. The seal 20 is then formed in the exposed section of the inner tube by heating the inner tube until it melts and collapses around the metal contact 18. Typically, this is done with a gas flame 26, as shown in FIG. 2C. After the seal is formed, the top section 12a of the outer tube is reattached to the lower section 12b. This may also be done with a gas flame, as shown in FIG. 2D.

There are several problems with the procedure described above for making the electrode. Fabricating the electrode assembly requires a great deal of skill and typically requires a glass worker with at least a year of experience in glass fabrication. Some skill is required to make a reliable seal between the inner tube and the metal contact. Reattaching the top section of the outer tube to the assembly requires even greater skill. The outer tube has a larger heat capacity than the inner tube because of its greater size, and it is easy to apply too much heat to the assembly when the top and bottom sections of the outer tube are fused. This can cause the filling solution to boil and burst the inner tube. The inner tube can soften and collapse before the outer tube is completely fused, and spacers are frequently necessary to prevent the inner tube from buckling. Great care must be taken to avoid an objectionable line where the top and bottom sections 12a and 12b are joined. Because of these problems, even experienced glass workers will produce an appreciable number of defective electrodes.

The improved method of the present invention for fabricating the electrode of FIG. 1 is shown in FIGS. 3A-3D. The process starts with an assembly of the inner tube 10, the outer tube 12, and the glass membrane bulb 14. This is shown in FIG. 2A. In the present invention, the inner tube 10 is made from a different material than the outer tube. The material of the inner tube is chosen so that it will absorb radiation energy at wavelengths which will pass through the outer tube with little or no absorption. Thus, when the assembly is illuminated with radiant energy of the proper wavelength, the radiant energy will pass through the outer tube and be absorbed by the inner tube. Various materials will serve this purpose. In the preferred embodiment, the outer tube is fabricated from a clear, potash-soda-lead glass, and the inner tube is fabricated from a glass which absorbs infrared radiation at frequencies which are transmitted by the outer tube, such as reed glass type 8512 or 8515 manufactured by the Schott Division of Jena Glass. These glasses are highly absorbant at a wavelength of 1.06 microns. Alternatively, the inner tube may be made of a colored glass which will absorb radiation of a wavelengths which are transmitted by the outer tube.

The inner tube is filled with the filling solution 16, and the metal contact 18 is inserted into the inner tube 10 until it is immersed in the filling solution. This is shown in FIG. 3C. Next, radiant energy of a wavelength absorbed by the inner tube is focused upon the inner tube at the point where the seal is to be formed. The radiant energy is absorbed very little or not at all by the outer tube, but is absorbed by the inner tube, causing the inner tube to melt and form the seal 20 around metal contact 18. This produces the finished electrode shown in FIG. 3D.

FIG. 4A shows the manner in which the electrode structure shown in FIGS. 2A and 3A is formed. The inner tube 10 and the outer tube 12 are first joined together as shown in FIG. 4A so that a small section of the inner tube projects from the bottom of the structure. Next the glass membrane bulb 14 is formed by dipping the end of the assembly shown in FIG. 4A into a crucible of molten membrane glass to attach a drop of glass on the end of the assembly. A glass blower then forms the membrane glass into a bulb 14 by blowing on the other end of the inner tube 10 until the molten glass expands to form the bulb, as shown by dotted lines 14a in FIG. 4A.

The energy radiated by the molten glass in the crucible includes radiation at the wavelengths absorbed by the inner tube 10 and transmitted by outer tube 12. Because of this, inner tube 10 may absorb much more of this energy and become much hotter than outer tube 12, and this can cause the joint betwwen the inner and outer tubes at location 13 to fracture. This problem may be worsened if the glasses of the inner and outer tubes have temperature expansion co-efficients which differ by a significant amount.

FIG. 4B illustrates one solution to this problem. In FIG. 4B, the inner tube 10 is fabricated from two kinds of glass. The lower portion 10a of the inner tube is fabricated from the same type of glass as the outer tube 12. The top portion 10b of the inner tube is made of glass which is absorbent of the desired radiant energy wavelengths. The two sections are joined at location 15 so that the absorbent glass portion 10b is present where the seal 20 is made.

The structure of FIG. 4B reduces the likelihood of a defective joint being caused by differential thermal expansion for two reasons. First, the joint between the two different glasses is moved farther away from the crucible of molten membrane glass during the time that the membrane bulb is being formed, thus reducing the energy absorbed by the absorbent glass section of the inner tube. Second, in the structure of FIG. 4B, the joint 15 between the two different glasses is a butt joint which is inherently stronger than the ring joint 13 where the inner and outer tubes meet, resulting in a lower likelihood of a fracture being caused by differential thermal expansion.

The present invention has many advantages over present methods of making electrodes. There is no longer any need to cut the outer tube into two sections, and the difficult process of reattaching the two sections of the outer tube is eliminated. The method of the present invention may be easily automated to eliminate event the minimal skill needed to form seal 20 with a gas flame. This allows the fabrication process to be performed by a person having a much lower technical ability. Additionally, the present invention results in a much lower percentage of defective electrodes than achieved with prior art methods.

FIG. 5 shows an apparatus which allows simple automation of the process shown in FIGS. 3. In FIG. 5, an electrode assembly which is ready to be sealed, such as that shown in FIG. 3B, is inserted into a holder 30. A source 28 of radiant energy at the wavelengths absorbed by the glass of inner tube 10 is positioned so that the energy is directed and focused on the inner tube 10 at the point where the seal 20 is to be made. Source 28 is controlled by a controller 48, as described below.

Holder 30 is attached to a rod 32 which passes through a bearing 34 mounted in a support 36. The lower end 38 of rod 32 is threaded and passes through a lower support 40. Lower support 40 is threaded so that rod 32 moves up and down as rod 32 is rotated. A motor 42 is connected to rod 32 by a belt 44 and pulleys 46 so that rod 32 is rotated by the motor. Motor 42 is controlled by controller 48.

In operation, an electrode assembly to be sealed is inserted into holder 30, and controller 48 is activated.

Controller 48 turns on energy source 28 and simultaneously activates motor 42 so that the rotation of the threaded portion of rod 32 lowers rod 32 and holder 30. The rotation of holder 30 and the electrode assembly aids in the even distribution of heat in inner tube 10 at the location where the seal is to be made. Additionally, outer tube 12 will generally absorb a small percentage of the energy from source 28, and the rotation minimizes hot spots in the outer tube 12 which might otherwise occur.

The seal between the inner tube and the metal contact is a mechanical seal, not an actual chemical bond between the materials. It has been found that moving the electrode assembly vertically over a distance of about one-fourth to one-half inch produces a more reliable seal. The electrode assembly must be moved in a downward direction while the seal is being formed. If the electrode moves upwards, the inner tube may burst as the glass is melted in a downwards direction towards the filling solution.

The source of radiant energy 28 may be implemented in various ways. The preferred glass for inner tube 10, made by Schott and discussed above, is highly absorbent at a wavelength of 1.06 microns. Tungsten filament bulbs radiate a large amount of energy in this range. In the preferred embodiment, source 28 is made of three tungsten lamps equally spaced around the electrode assembly with parabolic reflectors focused at the point where the seal is to be formed. A YAG laser will also serve as an energy source for radiation of this wavelength. Other sources will be apparent to those in the art.

The apparatus shown in FIG. 5 may be operated by a person having minimal training. The only actions which the operator must take are inserting the electrode assembly into holder, turning on controller 48, and removing the electrode assembly after the seal is completed. Additionally, as mentioned above, even when operated by unskilled operators, the present invention results in a lower percentage of defective electrode assemblies when compared with prior art fabrication methods employing highly skilled glass workers.

There has been described a new electrode structure especially adapted for the measurement of ion concentration and a method of manufacturing the new electrode, both of which have advantages over the prior art. It should be appreciated that the teachings of the present invention are applicable to sensors other than the ion selective electrodes described. Furthermore, modifications to the preferred embodiments described herein may be made by those of ordinary skill in the art in practicing the invention. The preferred embodiments described herein are only illustrative of the present invention and should not be construed as a limitation on the present invention. Rather, the invention should be interpreted in accordance with the following claims.

What is claimed is:

1. A fluid electrode, comprising:
    an inner tube, including a hollow glass tube formed of a glass which absorbs electromagnetic radiation of selected wavelengths, said inner tube having a bottom end which is closed by a membrane glass;
    an outer tube having top and bottom ends and formed of a second glass which is substantially transparent to said selected wavelengths;
    the inner tube being located within and parallel to the outer tube and being attached at its bottom end to the bottom end of the outer tube;
    the inner tube being filled with a filling solution to a level below the top end of the outer tube;
    a metal contact extending into the top end of the inner tube to provide an electrical contact to the filling solution; and
    a seal between the inner tube and the metal contact located below the top of the outer tube and formed by irradiating the inner tube with electromagnetic radiation of said selected wavelengths at the location of the seal until the inner tube melts and collapses around the metal contact to form said seal.

2. The article of claim 1 wherein the inner tube further comprises a tube of said first glass type connected to a tube of said second glass type to form a continuous tube, the bottom section of which is made of the second glass type and the top section of which is made of the first glass type;
    wherein the seal is located in the top section of the inner tube; and
    wherein the outer tube is connected to the bottom section of the inner tube.

3. The article of claim 2 wherein the inner tube further includes a bulb formed at the bottom of the inner tube by dipping the bottom of the inner tube into molten glass and blowing the bulb so that it closes the bottom end of the inner tube so that the inside of the bulb is filled with filling solution.

4. The article of claim 3 wherein the bulb is formed of an ion-selective membrane glass.

5. A method of making a fluid electrode, comprising the steps of:
    forming an inner tube, including a hollow glass tube formed of a first type of glass which absorbs electromagnetic radiation of selected wavelengths, said inner tube having a bottom end which is closed;
    forming an outer tube having top and bottom ends and formed of a second type of glass which is substantially transparent to radiation of said selected wavelengths;
    locating the inner tube within and parallel to the outer tube and attaching the bottom end of the outer tube to the inner tube near the bottom end thereof;
    filling the inner tube with a filling solution to a lever below the top end of the outer tube;
    inserting a metal contact into the top end of the inner tube to provide an electrical contact to the filling solution; and
    forming a seal between the inner tube and the metal contact at a location below the top of the outer tube by irradiating the inner tube through the outer tube with electromagnetic radiation of said selected wavelengths at the location of the seal until the inner tube melts and collapses around the metal contact to form said seal.

6. The method of claim 5 wherein the step of forming said inner tube further includes the steps of:
    closing the bottom end of the inner tube by dipping the bottom end into molten glass; and
    forming a bulb at the end of the inner tube by blowing the molten glass so that the bulb is contiguous with the inner tube whereby the step of filling fills the bulb and inner tube.

7. The method of claim 6 wherein the step of forming the inner tube further comprises the step of
    attaching a tube of said first glass type to a tube of said second glass type to form a continuous tube, the bottom section of which is made of the second glass type and the top section of which is made of the first glass type; and wherein the seal is located in the top section of the inner tube and the step of forming the seal further includes the step of irradiating the top section of the inner tube.

8. The method of claim 7 wherein the step of attaching the outer tube to the inner tube is performed before the step of forming the bulb.

9. The method of claim 5 wherein the step of forming the seal includes the step of rotating the inner tube about its own axis during said step of irradiating.

10. The method of claim 9 wherein the step of forming the seal further includes the step of moving the inner tube downward along its axis with respect to the electromagnetic radiation so that said seal between the inner tube and the contact is formed over a vertical interval.

11. The method of claim 9 wherein the step of forming the seal further includes the step of moving the inner tube downward along its axis with respect to the electromagnetic radiation for a distance of between approximately one-fourth to one-half inch so that said seal between the inner tube and the contact is formed over a vertical interval of between approximately one-fourth to one-half inch.

12. The method of claim 5 wherein the step of irradiating includes the step of focusing illumination from an incandescent light source on the inner tube at the location of the seal.

13. The method of claim 5 wherein the step of irradiating includes the step of focusing illumination from a tungsten light with a parabolic reflector on the inner tube at the location of the seal.

14. A fluid electrode formed by the process of:
forming an inner tube, including a hollow glass tube formed of a first type of glass which absorbs electromagnetic radiation of selected wavelengths, said inner tube having a bottom end which is closed;
forming an outer tube having top and bottom ends and formed of a second type of glass which is substantially transparent to radiation of said selected wavelengths;
locating the inner tube within and parallel to the outer tube and attaching the bottom end of the outer tube to the inner tube near the bottom end thereof;
filling the inner tube with a filling solution to a level below the top end of the outer tube;
inserting a metal contact into the top end of the inner tube to provide an electrical contact to the filling solution; and
forming a seal between the inner tube and the metal contact at a location below the top of the outer tube by irradiating the inner tube through the outer tube with electromagnetic radiation of said selected wavelengths at the location of the seal until the inner tube melts and collapses around the metal contact to form said seal.

15. The article of claim 14 wherein the step of forming said inner tube further includes the steps of:

closing the bottom end of the inner tube by dipping the bottom end into molten glass; and
forming a bulb at the end of the inner tube by blowing the molten glass so that the bulb is contiguous with the inner tube whereby the step of filling fills the bulb and inner tube.

16. The article of claim 15 wherein the step of forming the inner tube further comprises the step of
attaching a tube of said first glass type to a tube of said second glass type to form a continuous tube, the bottom section of which is made of the second glass type and the top section of which is made of the first glass type; and
wherein the seal is located in the top section of the inner tube and the step of forming the seal further includes the step of irradiating the top section of the inner tube.

17. The article of claim 14 wherein the step of forming the seal includes the step of rotating the inner tube about its own axis during said step of irradiating.

18. The article of claim 17 wherein the step of forming the seal further includes the step of moving the inner tube downward along its axis with respect to the electromagnetic radiation so that said seal between the inner tube and the contact is formed over a vertical interval.

19. For use with a fluid electrode assembly of the type having: an inner glass tube which is closed at the bottom end and made of a first type of glass which absorbs radiation at selected wavelengths and which contains a filling solution, a metal contact inserted in the top end of the inner tube to provide electrical contact to the filling solution, and an outer tube made of a second type of glass which is transparent to radiation at the selected wavelengths, the inner tube being located inside and parallel to the outer tube and the inner and outer tubes being connected near the bottom ends thereof; apparatus for making a seal between the metal contact with the inner tube at a predetermined location comprising:
means for rotating the electrode assembly about the axis of the inner tube;
heating means for providing radiation at said selected wavelengths, the radiation having sufficient energy to cause said inner tube to melt;
support means for positioning said heating means with respect to the means for rotating so that the radiation provided by the heating means is directed upon the inner tube at the location where the seal is to be made so as to melt the inner tube to form said seal;
the means for rotating further including means, operative when the means for rotating is rotating the electrode assembly, for moving the electrode along said axis in a downward direction towards the bottom thereof relative to said radiation, whereby the seal is extended upwardly along the inner tube towards the top of the electrode.

20. The apparatus of claim 14 wherein the means for providing radiation includes one or more tungsten filament light sources, and means for focusing heat from said one or more light source on the inner tube at the location of the seal.

* * * * *